US011857222B1

United States Patent
Leff et al.

(10) Patent No.: US 11,857,222 B1
(45) Date of Patent: Jan. 2, 2024

(54) MODULAR SCREW HEAD ASSEMBLIES

(71) Applicant: GLOBUS MEDICAL, INC., Audubon, PA (US)

(72) Inventors: David Leff, Philadelphia, PA (US); Matthew Bechtel, Philadelphia, PA (US); Caelan Allen, Philadelphia, PA (US); George Yacoub, Egg Harbor Township, NJ (US)

(73) Assignee: Globus Medical Inc., Audubon, PA (US)

( * ) Notice: Subject to any disclaimer, the term of this patent is extended or adjusted under 35 U.S.C. 154(b) by 0 days.

(21) Appl. No.: 17/842,970

(22) Filed: Jun. 17, 2022

(51) Int. Cl.
*A61B 17/70* (2006.01)
*A61B 17/68* (2006.01)

(52) U.S. Cl.
CPC ...... *A61B 17/7032* (2013.01); *A61B 17/7037* (2013.01); *A61B 17/7082* (2013.01); *A61B 2017/681* (2013.01)

(58) Field of Classification Search
CPC ........... A61B 17/77032; A61B 17/7034–7035; A61B 17/7037–7038
See application file for complete search history.

(56) References Cited

U.S. PATENT DOCUMENTS

| | | | |
|---|---|---|---|
| 9,924,975 B2 | 3/2018 | Jackson et al. | |
| 10,258,385 B1* | 4/2019 | Doubler | A61B 17/7037 |
| 10,806,495 B2 | 10/2020 | Jackson et al. | |
| 10,864,090 B2 | 12/2020 | Santiago et al. | |
| 2007/0270807 A1* | 11/2007 | Armstrong | A61B 17/7037 606/328 |
| 2008/0015579 A1* | 1/2008 | Whipple | A61B 17/7037 606/250 |
| 2008/0015597 A1* | 1/2008 | Whipple | A61B 17/7037 606/250 |
| 2010/0125302 A1* | 5/2010 | Hammill, Sr. | A61B 17/7035 606/301 |
| 2015/0201972 A1* | 7/2015 | Doubler | A61B 17/7002 606/266 |
| 2019/0183536 A1* | 6/2019 | May | A61B 17/7037 |

* cited by examiner

*Primary Examiner* — Eduardo C Robert
*Assistant Examiner* — Michelle C Eckman

(57) ABSTRACT

Orthopedic fixation devices, assemblies, and methods for securing a spinal rod. The orthopedic fixation device may include a tulip head with one or more internal components configured to secure a bone fastener. The tulip head may house a breakable shear clip that has an initial solid form. When the bone fastener is loaded into the tulip head, the shear clip breaks forming a split ring that expands radially outward to accept the screw head. Then, the shear clip collapses around the screw head, thereby securing the bone fastener to the tulip head. A spinal rod may be secured in the tulip head, for example, with a locking cap.

14 Claims, 17 Drawing Sheets

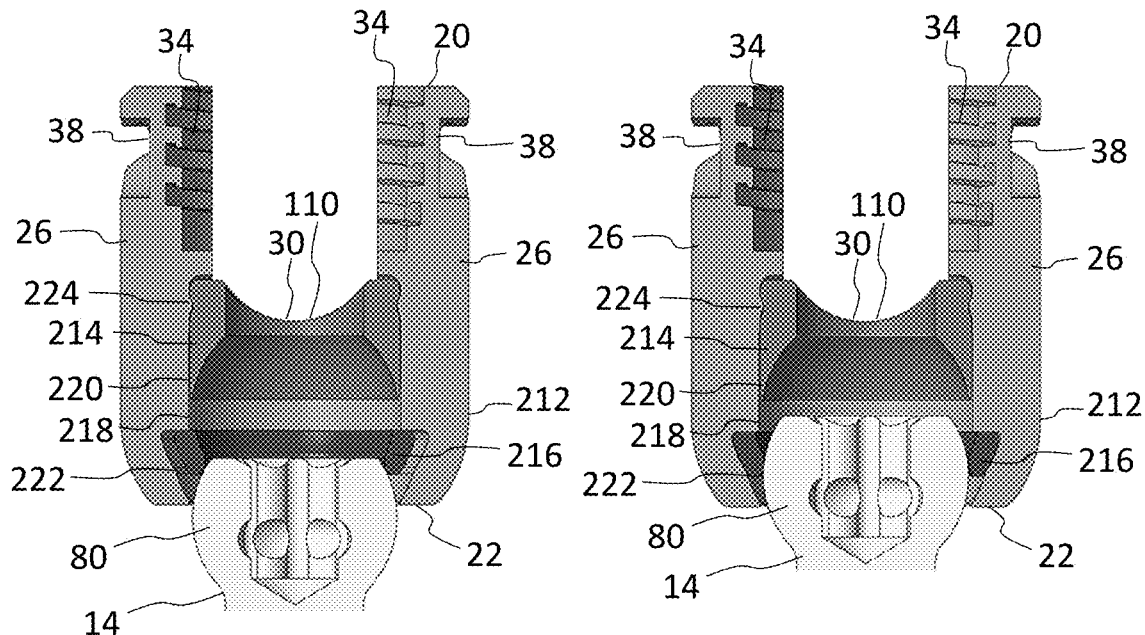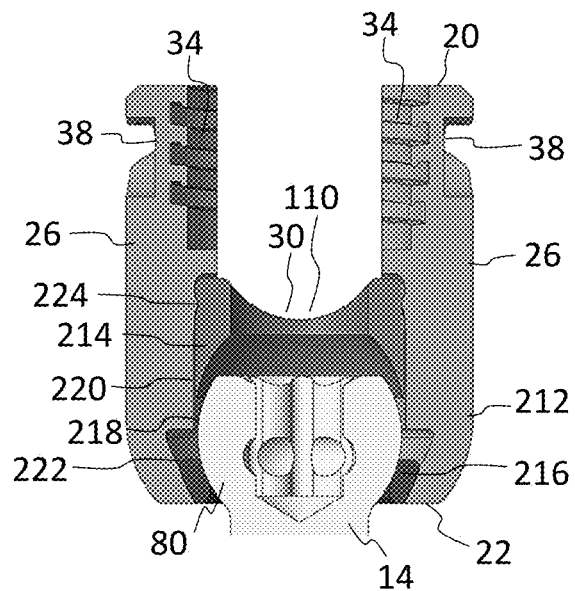
FIG. 8A  FIG. 8B
FIG. 8C

MODULAR SCREW HEAD ASSEMBLIES

FIELD OF THE INVENTION

The present application relates generally to orthopedic fixation devices, and more particularly, bone fastener assemblies, for example, for spine surgery.

BACKGROUND OF THE INVENTION

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. This treatment typically involves affixing a bone fastener to one or more vertebrae and connecting the bone fastener(s) to an elongate spinal rod that stabilizes members of the spine.

The bone fixation device may include a tulip head for coupling the bone fastener to the elongate spinal rod. A locking cap may be used to secure the elongate spinal rod in the tulip head. There exists a need for improved functionality, strength, and/or ease of manufacturing of the bone fastener components.

SUMMARY OF THE INVENTION

To meet this and other needs, bone fastener devices, assemblies, systems, and methods of treating spinal irregularities are provided. The bone fastener may include a tulip head with a locking cap for securing the spinal rod therein. The bone fastener may be configured for use with a variety of screws, such as polyaxial, uniplanar, monoaxial, reduction, modular, etc. The bone fastener may be implanted, for example, in open, semi-open, or percutaneous approaches to the posterior spine.

According to one embodiment, an orthopedic fixation assembly includes a tulip head, a saddle, a bearing washer, a shear clip, and a support clip. The tulip head has two arms defining a rod slot therebetween and a bore extending therethrough. The saddle is receivable in the bore of the tulip head. The saddle has an upper surface defining a rod seat aligned with the rod slot. The bearing washer is positionable below the saddle. The shear clip is positionable over the bearing washer. The support clip is configured to retain the shear clip in the tulip head. The shear clip is breakable at a fracture site upon application of a force.

The assembly may include one or more of the following features. The shear clip may have three states: an initial solid form, an expanded form after the shear clip breaks, and a collapsed form. In the initial solid form, the shear clip may be a full ring with partial slits defining a temporary bridge portion. In the expanded form after the shear clip breaks, the bridge portion breaks, thereby separating the full ring into a split ring radially expanded outward. In the collapsed form, the split ring collapses and springs closed. The bearing washer may be configured to center the shear clip within the tulip head to limit translation. The bearing washer may include a split ring with a radial neck protruding outward from the split ring. The support clip may include a split ring configured to fit in an internal groove at a bottom of the tulip head.

According to one embodiment, an orthopedic fixation assembly includes a tulip head, a breakable shear clip, and a bone fastener. The tulip head has two arms defining a rod slot therebetween. Each of the arms defines a threaded portion along an interior surface. The tulip head has a bore extending therethrough. The breakable shear clip is positioned in the bore of the tulip head. The bone fastener includes a screw head receivable in the tulip head and a shaft configured for engaging bone. The breakable shear clip has an initial solid form. When the bone fastener is loaded into the tulip head, the shear clip breaks forming a split ring that expands radially outward to accept the screw head. Then, the shear clip collapses around the screw head, thereby securing the bone fastener to the tulip head.

The assembly may include one or more of the following features. The bearing washer may be housed in an internal groove in the tulip head. The bearing washer may include a split ring with a radial neck protruding outward from the split ring and a plurality of slits defined through the top of the neck downward into the split ring. The initial solid form of the shear clip may be a full ring defining an inner seat for receiving the bearing washer and a pre-defined fracture site configured to break upon application of a force by the bone fastener. The support clip may be used for retaining the shear clip within the tulip head. The support clip may include a split ring defining a seat for the shear clip. After the shear clip collapses around the screw head, the shear clip may rest in the seat of the support clip and press against the screw head. The saddle may have an upper surface defining a rod seat and lower portion configured for receiving the screw head. The locking cap may have an outer body defining a thread. The locking cap is threadable between the two arms of the tulip head to secure a rod therein. When the locking cap is threaded downwardly onto the rod, the rod pushes against the rod seat of the saddle, and the saddle secures the bone fastener.

According to another embodiment, a method of installing an orthopedic fixation device may include one or more of the following steps in any suitable order: (1) providing an implant including a tulip head having two arms defining a rod slot therebetween, and a saddle, a bearing washer, a breakable shear clip, and a support clip housed in the tulip head; and (2) inserting a bone fastener having a head into a bottom of the tulip head such that (a) the head pushes the shear clip upward until the shear clip tops out on the bearing washer, (b) when enough upward pressure is placed on the shear clip, the shear clip fractures, allowing the shear clip to radially expand and accept the head, and (c) as the head continues to travel upwardly into contact with the saddle, the shear clip collapses around the head, thereby securing of the bone fastener. The bone fastener may be inserted into the tulip head intra-operatively. The method may further include: (3) positioning a rod between the two arms and into the rod slot of the tulip head; and (4) threading a locking cap downwardly between the two arms of the tulip head, wherein the rod presses against a rod seat of the saddle, and the saddle presses against the head of the bone fastener, thereby securing the rod and bone fastener.

According to another embodiment, an orthopedic fixation assembly includes a tulip head, a saddle, a retaining clip, and a bone fastener. The tulip head has two arms defining a rod slot therebetween and a bore extending therethrough. The saddle is receivable in the bore of the tulip head. The saddle has an upper surface defining a rod seat aligned with the rod slot. The retaining clip is located at a bottom of the tulip head. The bone fastener has a head receivable in the tulip head, through the retaining clip, and into the saddle. The bone fastener is a uni-planar screw allowing for angulation in a single direction.

The uni-planar assembly may include one or more of the following features. The tulip head may pivot on the head of the bone fastener to allow for medial-lateral angulation. The head of the bone fastener may include spherical surfaces in a direction of angulation and flat opposing surfaces parallel to the direction of angulation. The flat surfaces of the head may align with corresponding flat surfaces inside the saddle. The flat surfaces of the head and inside the saddle may restrict rotation of the bone fastener about a central axis of the tulip. The orientation of the flat surfaces of the head and saddle may be parallel to the rod slot to allow for coronal and axial corrections. The orientation of the flat surfaces of the head and saddle may be perpendicular to the rod slot to allow for sagittal corrections. Opposite sides of the saddle may have flat surfaces configured to mate with corresponding flat surfaces inside the tulip head, thereby restricting the saddle from angling within the tulip head. The retaining clip may include a split ring configured to fit in an internal groove in the tulip head and around a bottom of the screw head.

According to another embodiment, an orthopedic fixation assembly includes a tulip head, a uni-planar bone fastener, a saddle, and a retaining clip. The tulip head has two arms defining a rod slot therebetween. Each of the arms defining an interior threaded portion along an inner surface. The tulip head has a bore extending therethrough. The uni-planar bone fastener includes a screw head receivable in the tulip head and a shaft configured for engaging bone. The saddle has an upper surface defining a rod seat aligned with the rod slot and a lower portion configured for receiving the screw head. The retaining clip is positioned in a groove in the tulip head and around a bottom of the screw head. The screw head has a plurality of flats aligned with corresponding flats in the lower portion of the saddle to restrict movement of the shaft relative to the tulip head to one direction.

The uni-planar assembly may include one or more of the following features. The assembly may further include a spinal rod receivable in the rod slot of the tulip head and the rod seat of the saddle, and a locking cap having an outer body defining an exterior thread such that the locking cap is threadable between the two arms of the tulip head to secure the spinal rod therein. When the locking cap is threaded downwardly onto the spinal rod, the spinal rod pushes against the seat of the saddle, and the saddle secures the bone fastener. The interior threaded portion of the tulip head may include downward projecting hooks and the exterior thread of the locking cap may include corresponding upward projecting hooks configured to intermesh. When threaded together, the downward and upward hooks form inward-facing surfaces, which point toward one another at each level of engagement.

According to yet another embodiment, an orthopedic fixation system may include a tulip assembly and an instrument. The tulip assembly includes a tulip head having two parallel arms defining a rod slot therebetween, each of the arms defining an interior threaded portion along an inner surface, an annular groove interrupted by a rocker hole along an outer surface, tower pockets along both sides of each arm, flats positioned on opposite sides of the tulip head below the rod slot, the tulip head having a bore extending therethrough, a saddle retained in the bore having an upper surface defining a rod seat aligned with the rod slot, and a retaining clip positioned in an interior groove at a bottom of the tulip head. The instrument is configured to grasp the tulip head. The instrument may be an inserter or rocker-style instrument, for example.

The system may include one or more of the following features. The annular groove may define an inward facing top surface to form an upper dovetail interface with the instrument. The rocker holes may be cylindrical or obround pockets configured to receive pins from the instrument to thereby lever and reduce a spinal rod into the tulip head. The tower pockets may include slots along the sides of each arm configured to receive protrusions from a sleeve of the instrument to prevent splay and disengagement of the instrument. The interior groove in the tulip head may have a spherical profile to allow the retaining clip to angle.

Also provided are kits including implants of varying types and sizes, rods, various instruments and tools, and other components for performing the procedure.

BRIEF DESCRIPTION OF THE DRAWINGS

A more complete understanding of the present invention, and the attendant advantages and features thereof, will be more readily understood by reference to the following detailed description when considered in conjunction with the accompanying drawings, wherein:

FIGS. 8A-8C show cross-sectional views of inserting the screw, with the clip expanded, and with the clip pulled down to secure the screw, respectively;

DETAILED DESCRIPTION OF THE INVENTION

Figure 1:
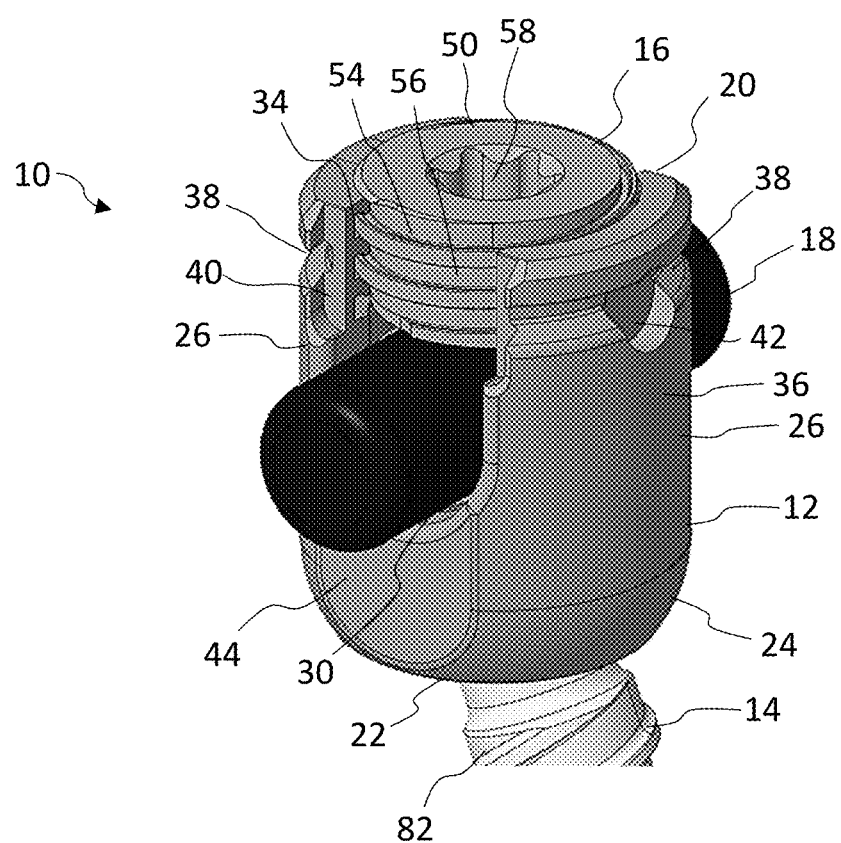
FIG. 1 is a perspective view of a rod secured in a modular screw head with a locking cap according to one embodiment.

Embodiments of the disclosure are generally directed to bone fastener devices, assemblies, systems, and methods for securing a bone fastener and/or spinal rod. Specifically, embodiments are directed to tulip assemblies configured to secure the spinal rod to the bone fastener. Although described with reference to the spine, it will be appreciated that the devices and systems described herein may be applied to other orthopedic locations and applications, such as trauma.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments of modifications thereof are contemplated as falling within the scope of this disclosure and equivalents thereto.

Referring now to FIGS. 1-5, an orthopedic fixation device, implant, or bone fastener assembly 10 is shown according to one embodiment. The implant or bone fastener assembly 10 may include a modular tulip element or tulip head 12 attachable to a bone fastener 14. The modular tulip 12 may be top loaded intra-operatively onto the bone fastener 14. The tulip head 12 is also configured to receive a locking cap 16 to secure a spinal rod 18 therein. For a polyaxial bone fastener 14, tightening the locking cap 16 compresses the rod 18 into the tulip head 12, thereby restricting motion of the bone fastener 14 and forming a rigid construct.

Figure 2:
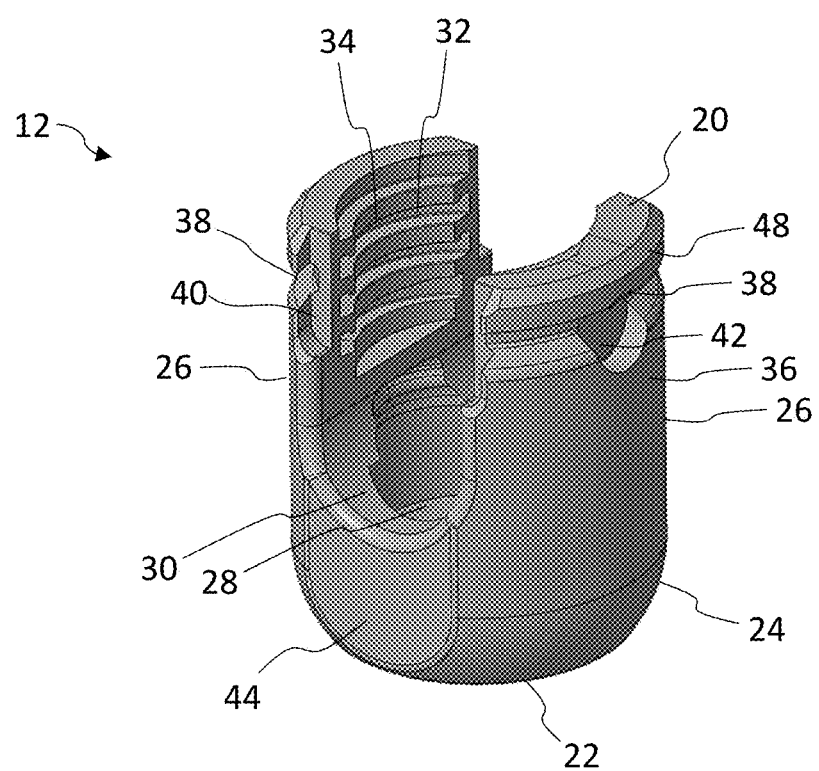
FIG. 2 shows a perspective view of a tulip head according to one embodiment.

With further emphasis on FIG. 2, the tulip head 12 extends from an upper surface or top 20 to a lower surface or bottom 22 along a central longitudinal axis. The tulip head 12 may include a base or body 24 and arms 26 that extend upwardly from the body 24. The arms 26 may be aligned generally in parallel with one another. A central bore 28 may extend through the body 24 of the tulip head 12. The opposed arms 26 may define a U-shaped channel or rounded rod slot 30, transverse to the bore 28. The rounded rod slot 30 is sized and configured to accept the rod 18 perpendicular to the threads of the locking cap 16. Each of the arms 26 has an interior surface 32 having a threaded portion 34 for engaging the locking cap 16.

Each of the arms 26 may include an outer surface 36 with one or more features for engagement with mating instruments. For example, instruments (such as instruments 230, 250, 260) may engage with these features to constrain the instrument axially to the tulip head 12. Each of the arms 26 may include a tool engagement groove 38 formed into the outer surface 36, which may be used for holding the tulip head 12 with a suitable tool. The groove 38 may include a cylindrical groove cut into the tulip head 12 with an inward facing top surface 46. The inward facing top surface 46 may have an inclined face that slopes such that it is lower toward the outer surface 36 and higher as the sloped surface 46 extends inward. An overhang 48 may form a bottom facing surface pointed toward the top facing surface 46. The bottom facing surface of the overhang 48 may also be slanted or sloped. For example, the bottom facing surface of the overhang 48 may have the same or similar slope to the upward facing surface 46. The annular groove 38 may form an upper dovetail configured for engaging with the instrument. The inward angle of the upper dovetail 38 may prevent the instrument from disengaging by directing forces on the instrument inward and maintaining engagement.

Each of the arms 26 may include a tower pocket 40 configured to engage with mating instruments to constrain rotation of the instrument to the tulip head 12. The tower pockets 40 may include slots adjacent to the rod slot 30. For example, a vertical slot may be provided along an upper portion of each side of the arms 26. The outward surfaces of the pockets 40 are configured to contact corresponding surfaces on the instrument, thereby preventing splay and disengagement of the instrument from the tulip head 12. The upper dovetail 38 and tower pockets 40 may be combined to fully constrain the instrument to the tulip head 12.

The outer surface 36 of each arm 26 may also define a ball hole or rocker hole 42. The rocker holes 42 may interrupt the engagement groove 38, for example, at a central position on each arm 26. The rocker holes 42 may be cylindrical or obround pockets which allow engagement of a rocker-style instrument with pin features, allowing rotation of the instrument within the holes 42. Rotation about the rocker holes 42 allows the user to lever and reduce the rod 18 into the head 12. In addition, front and back surfaces 44 of the tulip body 24 may be flat or planar. The flats 44 may be positioned on opposite sides of the tulip body 24, for example, below the rod slot 30. The flats 44 may act as an additional counter-rotation feature when engaged with an instrument.

The rod 18 may be secured in the tulip head 12 with the locking cap 16. The locking cap 16 may include a body with an upper surface 50, a lower surface 52, and an outer body 54 defining a threaded portion 56. As shown in FIG. 1, the locking cap 16 may be in the form of a set screw with a drive feature or recess 58 defined in the upper surface 50 configured to be engaged by a driving instrument, which is able to insert and tighten the locking cap 16 in the tulip head 12. The recess 58 may be a hexalobe, slot, cross, or other suitable shape that may engage with a tool or device having a corresponding tip. The recess 58 may extend partially into the body of the locking cap 16 or entirely through the locking cap 16. The bottom 52 of the locking cap 16 may be flat or otherwise configured to ensure desired contact with the rod 18.

The external threaded portion 56 of the locking cap 16 may have a thread geometry configured to secure the locking cap 16 to the tulip head 12. The external threaded portion 56 of the locking cap 16 may extend between the upper and lower surfaces 50, 52. The internal threads 34 within the head 12 mate with external threads 34 of the locking cap 16. Tightening the locking cap 16 compresses the rod 18 into the head 12 and internal components, thereby restricting motion of the screw 14 and forming a rigid construct.

Figure 3:
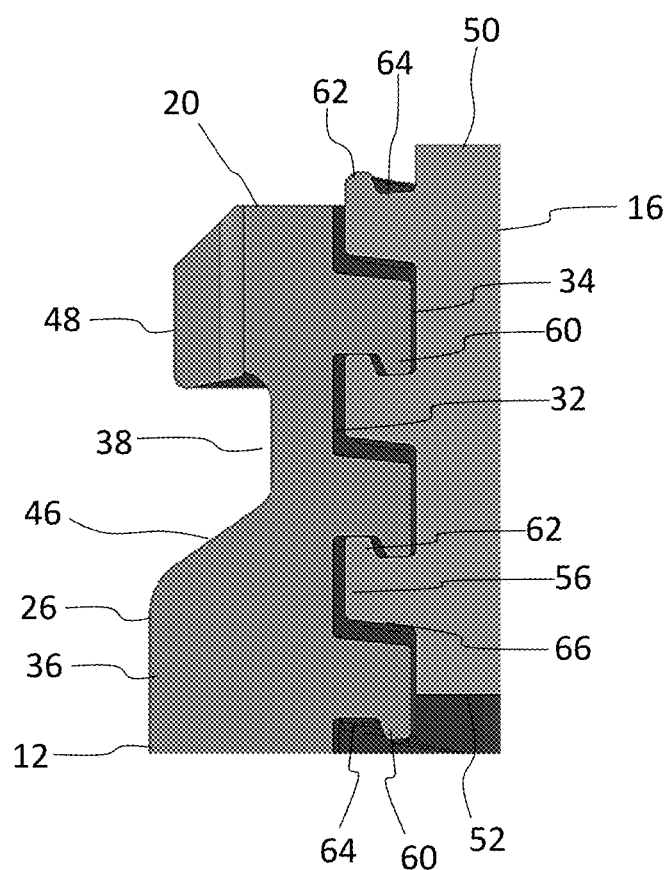
FIG. 3 shows a close-up cross-sectional view of the threaded engagement between the locking cap and the tulip head according to one embodiment.

In one embodiment shown in FIG. 3, the threads 34, 56 of the locking cap 16 and tulip head 12 may be configured to intermesh to prevent or reduce splaying of the arms 26 of the tulip 12. In one embodiment, the interior threads 34 of the tulip 12 have a downward projecting hook 60 and the exterior threads 56 of the locking cap 16 have a corresponding upward projecting hook 62. It will be appreciated that these orientations may be reversed. When threaded together, the downward and upward hooks 60, 62 form inward-facing surfaces, which point toward one another at each level of engagement. The inward-facing surfaces 60, 62 may be vertical or slightly angled out for ease of manufacturing. The threads 34, 56 may each define a contacting surface 64 where the opposite hook 60, 62 is receivable when threaded together. For example, the cap 16 may have a contacting top surface 64 and the tulip 12 may have a contacting bottom surface 64, which receive the respective hooks 60, 62. The contacting surfaces 64 may be horizontal or slightly angled out. Corner radii may be added to each outer and inner corner of the threads 34, 56 to prevent edge loading and for ease of manufacturing. The flank surface 66 of the threads 56 may be angled outward to increase the root height of the threads 56 for strength or may be horizontal. The thread profile may provide for increased splay resistance, strength, and resistance to cross-threading of the locking cap 16 in the tulip head 12. The anti-splay features in the thread geometry and angular profile of the threads may prevent or minimize mis-engagement.

When tightened, an upward force is exerted on the bottom of the locking cap 16 by the rod 18, causing the top surface 64 of the threads 56 to come into contact. As the tightening torque increases, significant forces are developed within the threads 34, 56, which may cause the tulip 12 to deflect outward and begin to splay. In the embodiment shown, the inward-facing surfaces 60, 62 of the external threads 56 of the locking cap 16 and internal threads 34 of the tulip 12 contact after the tulip 12 begins to splay. These inward-facing surfaces 60, 62 develop forces which counter the splaying action and prevent further splay. The locking cap 16 may include any suitable thread geometry, for example, to improve strength, reduce outward splaying forces on the tulip head 12, increase resistance to cross-threading, allow quick engagement of the locking cap 16, and/or maintain a more consistent interface with mating instruments.

The bone fastener 14 may include a bone screw, anchor, clamp, or the like configured to engage bone. In one embodiment, the bone fastener 14 is a bone screw, such as a pedicle screw, having a screw head 80 and a threaded shaft 82 extending from the screw head 80. The figures do not show the distal end of the threaded shaft 82, but suitable bone fasteners 14 will be recognized by those of ordinary skill in art. Examples of bone fasteners, other implants, and rod constructs are described in more detail, for example, in U.S. Pat. No. 10,368,917, which is incorporated by reference herein in its entirety for all purposes. It will be appreciated that the threaded shaft 82 may have a number of different features, such as thread pitch, shaft diameter to thread diameter, overall shaft shape, and the like, depending, for example, on the particular application. While the screw head 80 may have any general shape, in the case of a polyaxial fastener 14, at least a portion of the screw head 80 may have a curved surface in order to allow for rotational movement and/or angular adjustment of the bone fastener 14 with respect to the tulip head 12. For example, at least a portion of the screw head 80 may be shaped to form a portion of a ball or at least a portion of a sphere. The screw head 80 may have a tool engagement surface 84 that can be engaged, for example, by a screw-driving instrument or other device. In one embodiment, the bone screw head 80 has a hexalobe recess 84 for driving the screw 14 into bone. It will be appreciated that any suitably shaped tool engagement surface 84 may be provided.

Figure 4:
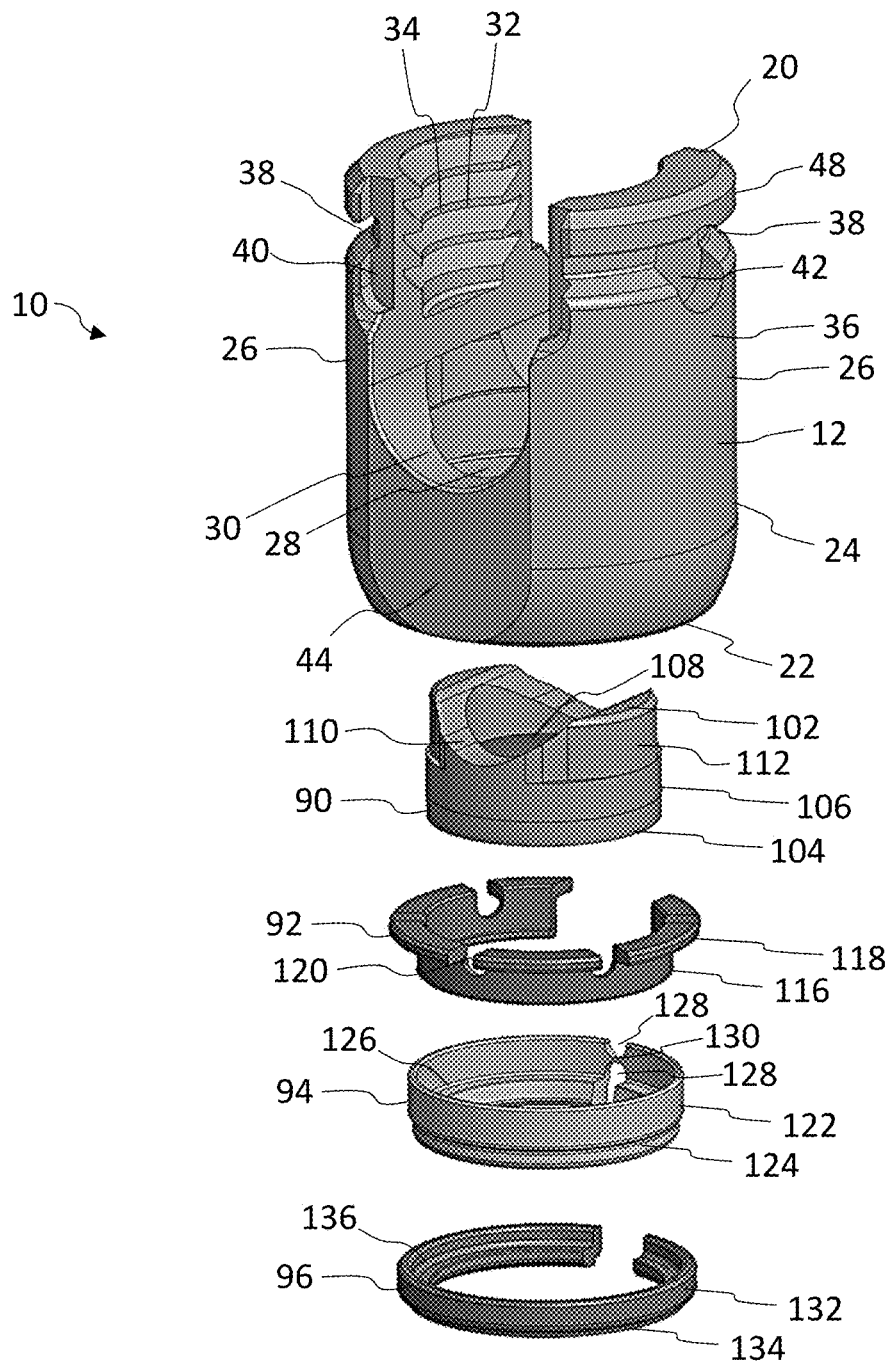
FIG. 4 shows an exploded view of a modular tulip assembly configured for retaining a screw and a spinal rod according to one embodiment.

Turning now to FIG. 4, an exploded view of a modular tulip assembly 10 is shown according to one embodiment. The modular tulip assembly 10 includes tulip head 12, a saddle 90, a bearing washer 92, a shear clip 94, and a support clip 96. The tulip head 12 houses all of the components 90, 92, 94, 96. The modular tulip assembly 10 may be top loaded intra-operatively onto the bone fastener 14. The spinal rod 18 may be secured into the tulip head 12 with the locking cap 16.

The saddle 90 applies compressive force to the bone screw 14 and restricts its angulation when the rod 18 is tightened to the implant 10 with the locking cap 16. The saddle 90 may have an upper surface 102, a lower surface 104, an outer surface 106, which may be curved or rounded, and a bore 108 defined through the saddle 90. A lower portion of the bore 108 may be rounded and sized to receive an upper portion of the screw head 80. A rod slot or seat 110 may be defined in the upper surface 92 of the saddle 90. The rod slot or seat 110 may be configured to receive a bottom portion of the rod 18 therein. The rod seat 110 may be generally aligned with the rod slot 30 through the tulip head 12. The saddle 90 may include one or more external recesses or channels 112. For example, the saddle 90 may include two opposed, recessed channels 112 positioned near the top of the saddle 90. The saddle 90 provides a collar about an upper portion of the screw head 80. The polyaxial motion of the screw 14 is locked when the locking cap 16 is threaded downwardly, compressing the rod 18 onto the saddle 90, which thereby compresses against the spherical head 80 of the bone screw 14.

The bearing washer 92 centers the shear clip 94 within the tulip head 12 to limit translation of the shear clip 94 within the tulip head 12, while also providing friction against the bone screw head 80 for memory. The bearing washer 92 may be housed in an internal groove in the tulip 12 and positioned around the bottom of the saddle 90. The bearing washer 92, saddle 90, and tulip head 12 may be coaxially aligned. The bearing washer 92 may include a split ring 116 with a central through opening and a wide cut in fluid communication with the central through opening. The bearing washer 92 includes a radial neck 118 protruding outward from the split ring 116. One or more slits 120 may be defined through the top of the neck 118 downward into the split ring 116. The slits 120 may be rounded with a circular or semi-circular cross-section. In the embodiment shown, three slits 120 are provided equally around the ring 116 although any suitable location and number of slits 120 may be provided.

The shear clip 94 retains the bone screw 14 within the assembly 10 and resists compressive force exerted down on the bone screw 14. The shear clip 94 is a breakable component configured to fracture when enough force is placed on the shear clip 94. Due to its breakable nature, the shear clip 94 has different forms throughout the procedure. During the initial assembly, the shear clip 94 is in an initial solid form. After the screw head 80 is forced through the shear clip 94, the shear clip breaks and is radially expanded to accommodate the head 80 of the screw 14. After breaking, the shear clip 94 collapses, acting like a spring around the screw head 80, and falls into its final position to secure the screw head 80 to the tulip head 12.

In its initial state, the shear clip 94 may be positionable in an internal groove in the tulip 12 and located around the split ring 116 of the bearing washer 92. As a solid member, the shear clip 94 may include a full ring 122 with a central through opening. The shear clip 94 is axially aligned with the tulip 12, the saddle 90, and the bearing washer 92. The shear clip 94 may include a lower annular ring 124 defining a groove along an outer surface and a rim along an inner surface of the clip 94. The inner rim of the lower annular ring 124 may define a seat 126 with the body of the clip 94, which is permitted to translate along the split ring 116 of the bearing washer 92.

The shear clip 94 may define a fracture site configured to break upon application of a force. In one embodiment, one or more partial slits 128 may be defined through the body of the ring 122. The slits 120 may be rounded with a circular, semi-circular, and/or obround cross-section, for example. The slits 120 may be vertically aligned to form a temporary bridge portion 130 completing ring 122 in its solid form. For example, the temporary bridge 130 may be a thin strip of material continuous with the material of the ring 122, which is configured to break when enough force is applied. In the embodiment shown, two aligned slits 130 are shown to define a single temporary bridge 130 through the clip 94 although any suitable location and number of slits 130 and/or bridges 130 may be provided. After a suitable force is applied to the shear clip 94 during use, the bridge portion 130 breaks, thereby separating the full ring 122 into a split ring. In this manner, the shear clip 94 may allow for three distinct states of bodies: solid (initial form), expanded (after breaking), and collapsed (around screw head 80), which allow for stronger head assembly and disassembly.

The support clip 96 may be provided to retain the shear clip 94 within the head 12 of the modular tulip assembly 10. The support clip 96 may be axially aligned with the tulip 12, the saddle 90, the bearing washer 92, and the shear clip 94. The support clip 96 may be positionable in an internal groove at the bottom of the tulip head 12 and located around the annular ring 124 of the shear clip 94. The support clip 96 may include a split ring 132 with a central through opening and cut in fluid communication with the central through opening. The support clip 96 may include a lower annular ring 134 defining a groove along an outer surface and a rim along an inner surface of the clip 96. The inner rim of the lower annular ring 134 may define a seat 136 within the body of the clip 96, which is permitted to translate along the annular ring 124 of the shear clip 94.

Figure 5A:
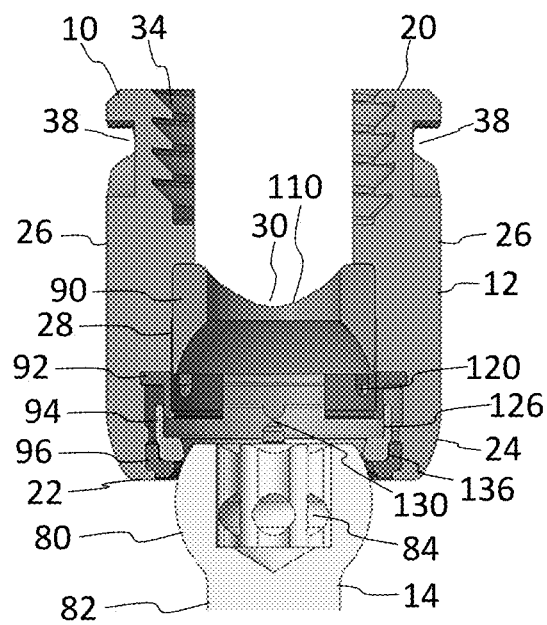
FIGS. 5A-5E show cross-sectional views of the modular tulip of FIG. 4 depicting intra-operative assembly of the screw head to the modular tulip.
Figure 5B:
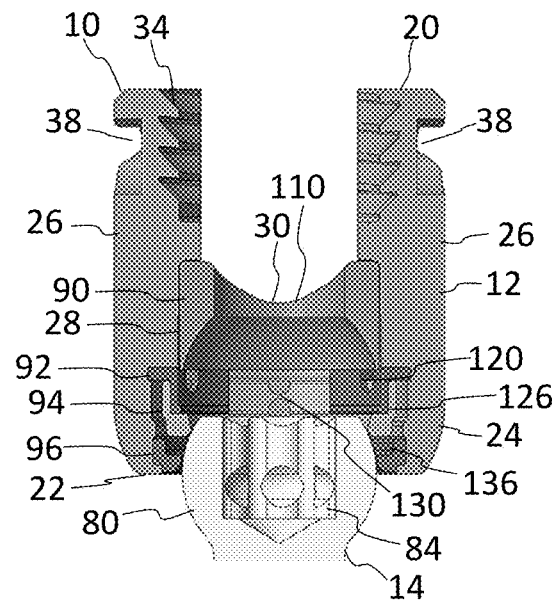

As best seen in FIGS. 5A-5E, the modular tulip 10 may be assembled to the top of the bone screw 14 intra-operatively. It will be appreciated that the shaft of the bone screw 14 is omitted for clarity. With reference to FIG. 5A, before the head 80 of the bone fastener 14 is loaded into the bottom of the tulip 12, the support clip 96 rests in the bottom of the tulip head 12. The annular ring 124 of the shear clip 94 rests in the seat 136 of the support clip 96. The temporary bridge 130 of the shear ring 94 is fully intact. The bearing washer 92 sits above the shear clip 94. The saddle 90 rests above the shear clip 94. FIG. 5A shows the screw head 80 beginning to pass through the bottom of the tulip 12, through the support clip 96, and into contact with the shear clip 94. FIG. 5B shows the screw head 80 pushing the shear clip 94 upward until the shear clip 94 tops out on the bearing clip 92. In this manner, the shear clip 94 lifts out of the support clip 96, and the split ring 116 of the bearing washer 92 is received into the seat 126 of the shear clip 94.

Figure 5C:
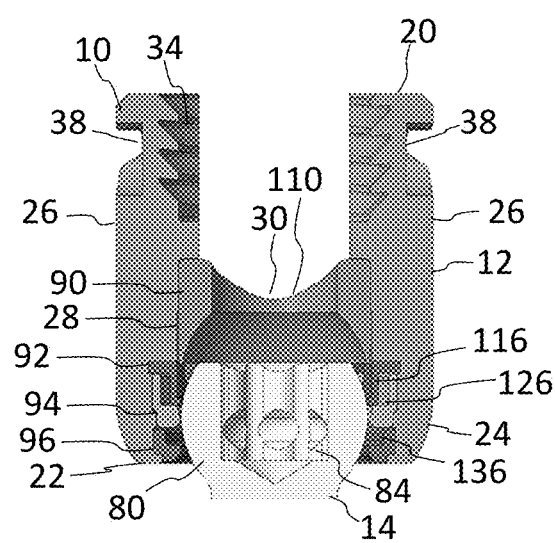
Figures 5D, 5E:
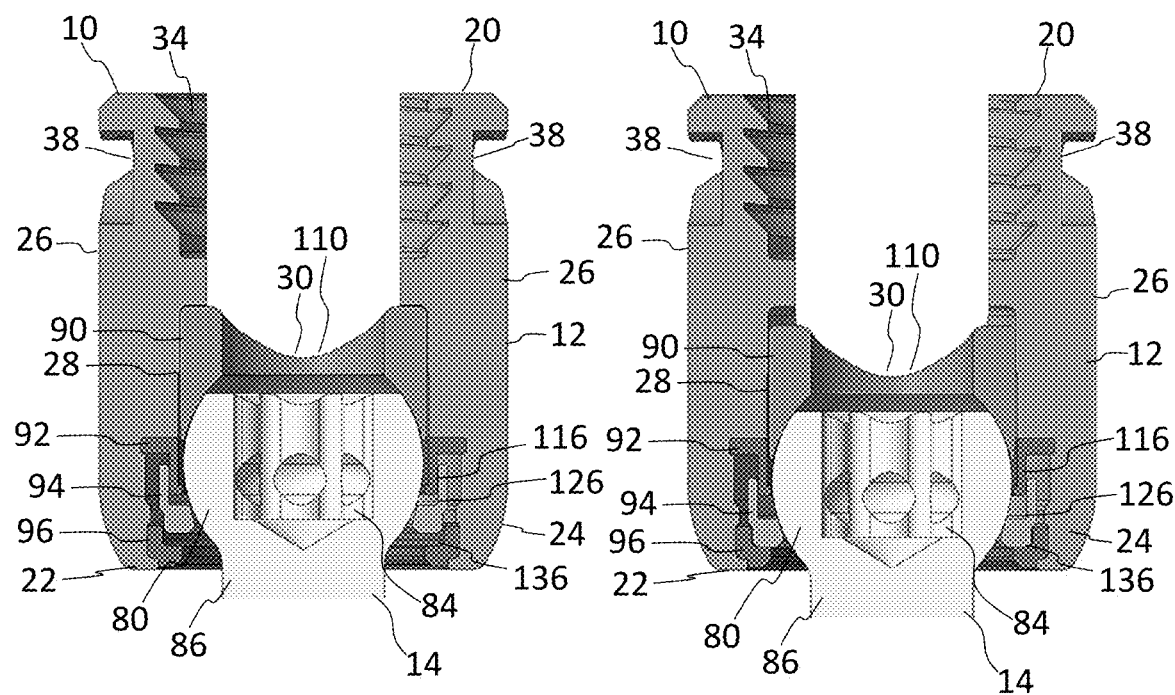
Figure 6A:
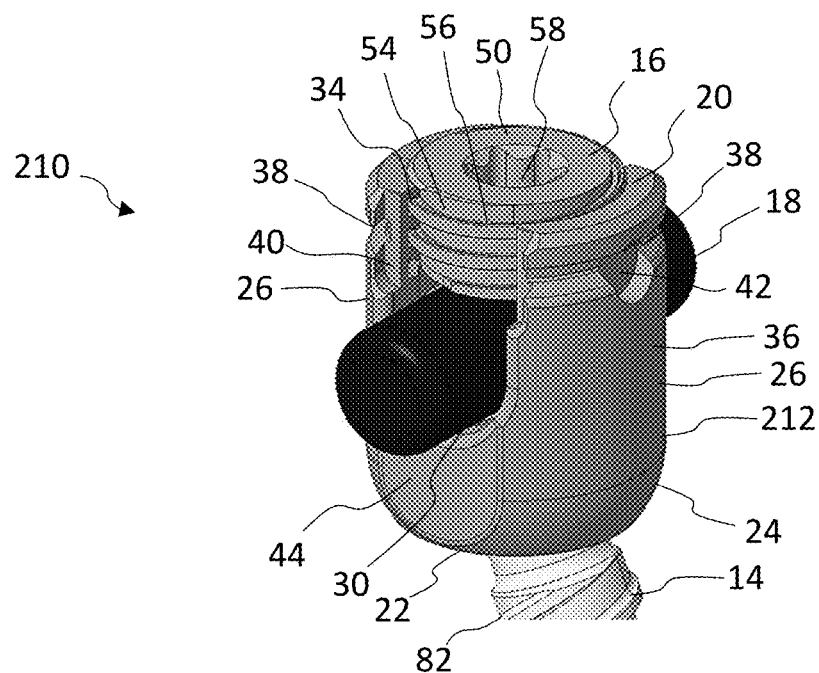
FIGS. 6A-6B depict perspective and cross-sectional views, respectively, of a modular assembly for retaining a rod and screw head according to another embodiment.
Figure 6B:
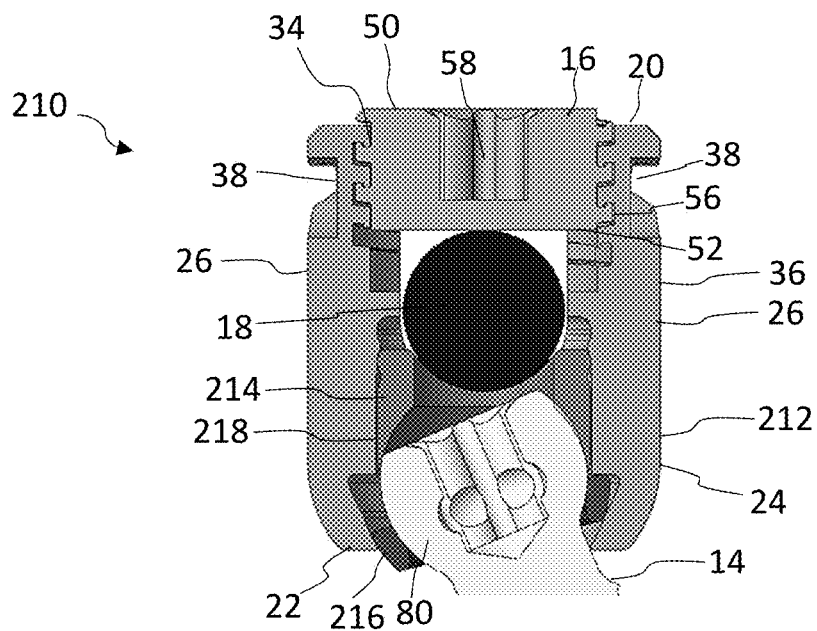

With emphasis on FIG. 5C, when enough upward pressure or force is placed on the shear clip 94, the shear clip 94 fractures at known site 130, allowing the shear clip 94 to expand and accept the bone screw head 80. The shear clip 94 surrounds the head 80 of the fastener 14. The shear clip 94 expands radially outward leaving a gap between the seat 126 and the ring 116 of the bearing washer 92. FIG. 5D shows the screw head 80 as it continues to travel upwardly into contact with the bottom of saddle 90. The shear clip 94 then collapses as a spring around the screw head 80 and falls in place to the internal diameter of the support clip 96 by following the position of the bearing clip 92. As shown in FIG. 5E, the annular ring 124 of the broken and collapsed shear clip 94 rests in the seat 136 in the support clip 96 and presses against the screw head 80. The top of the broken ring 122 of the shear clip 94 presses against the split ring 116 of the bearing washer 92. The saddle 90 translates downward and is positioned around the top of the screw head 80. The saddle 90 may be located between the top of the bearing washer 92 and the screw head 80. The broken and collapsed shear clip 94 is configured to accept the load of the screw head 80 and saddle 90 when loaded by rod 18 via locking cap 16.

Turning now to FIGS. 6-9, a modular tulip assembly 210 for retaining screw head 80 and spinal rod 18 is shown according to another embodiment. Tulip assembly 210 is similar to tulip assembly 10 except the internal components include a saddle 214 and clip 216 to retain the bone fastener 14. Similar to tulip 12, tulip head 212 has many of the same features including opposed arms 26 defining U-shaped rod slot 30 configured to accept the rod 18, interior threaded portions 34 for engaging the locking cap 16, and one or more outer engagement features 38, 40, 42, for interaction with mating instruments. The modular tulip assembly 210 also features a flat surface 44 on opposing sides of the tulip assembly.

The saddle 214 includes an upper surface for receiving the rod 18 and a bottom surface for receiving the top of the screw head 80. The clip 216 may include a loop, ring, split-ring, snap ring, or other suitable retaining ring. In an exemplary embodiment, the clip 216 is a split retaining clip. The inner bore 218 defines a first upper portion 220 above a second lower portion 222. The saddle 214 is housed within the upper portion 220 and the clip 216 is housed within the lower portion 222 with excess clearance to allow them each to travel along the central axis of the tulip 212.

The upper portion 220 may include a modular bump 224 configured to interface with a corresponding recess in the saddle 214. For example, when the saddle 214 is in a fully upward position, the inner bump 224 is receivable in the corresponding radial recess around the saddle 214, thereby securing the saddle 214 in the tulip head 212. The lower portion 222 that the clip 216 is housed within may taper such that the bottom of portion 222 has minimal clearance over the clip 216 while the top of portion 222 has additional clearance. In one embodiment, the outer surface of the clip 216 and the inner surface 222 of the tulip 212 is conically tapered. In an alternative embodiment, the outer surface of the clip 216 is spherically tapered, and the recess 222 in the inner surface of the tulip 212 has two radiused tapers so that the clip 216 can angle or tilt with the screw 14.

Figure 7A:
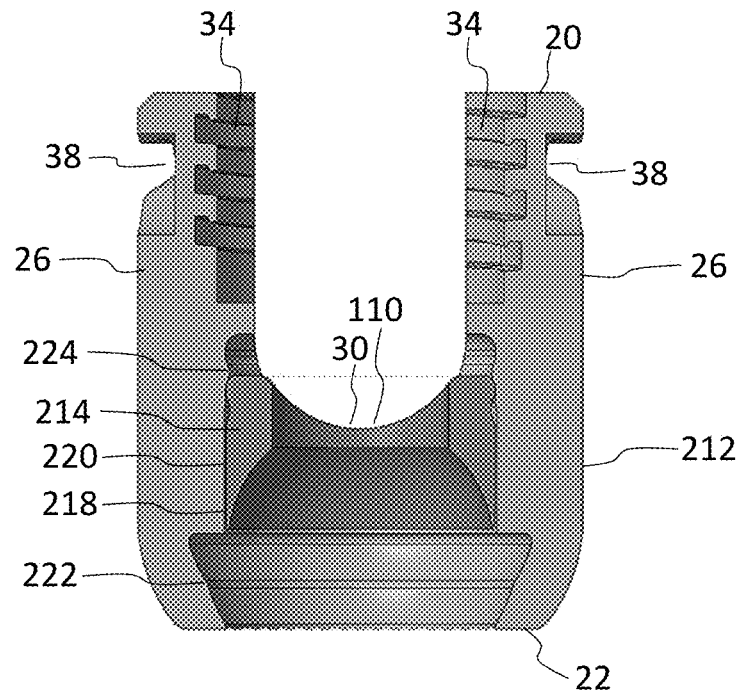
FIGS. 7A-7B show cross-sectional views of saddle and clip insertion into the tulip head, respectively.
Figure 7B:
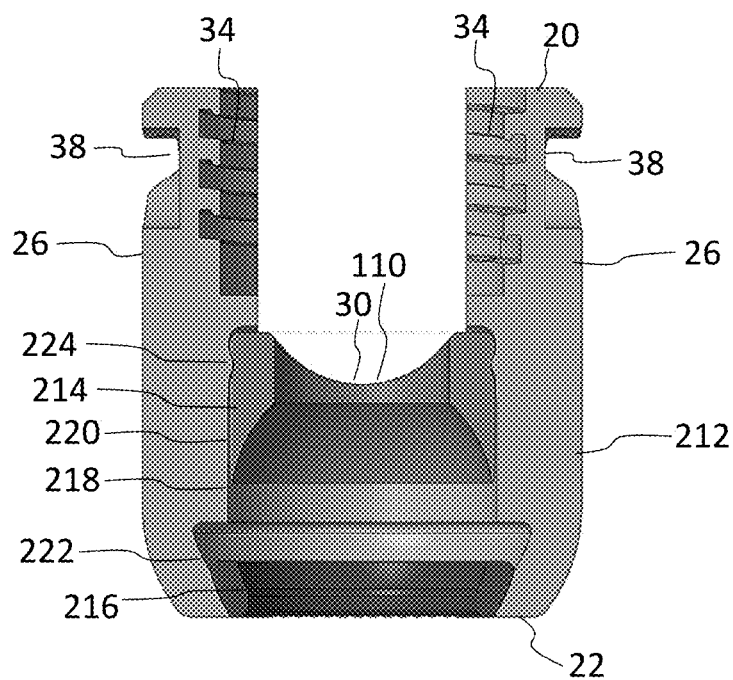

With further emphasis on FIGS. 7A-7B, the saddle 214 and clip 216 may be assembled into the tulip head 212, for example, through the bottom 22 of the tulip head 212. As shown in FIG. 7A, assembly may involve insertion of the saddle 214 from the lower portion of the tulip head 212 and into bore 220. As shown in FIG. 7B, the saddle 214 is raised past modular bump 224 so that the saddle 214 is retained in an upward position. The split retaining clip 216 is then inserted into the groove 222 in the lower portion of the tulip head 212.

Turning now to FIGS. 8A-8C, modular screw insertion is shown according to one embodiment. As shown in FIG. 8A, when the spherical head 80 of the modular screw 14 is inserted into the lower bore of the tulip 212, the head 80 contacts the bottom of the clip 216 and moves the clip 216 to the upper portion of the clip groove 222. As shown in FIG. 8B, further insertion of the spherical head 80 expands the clip 216. The additional clearance of the groove 222 allows the clip 216 to expand until the center of the spherical head 80 of the screw 14 has passed through the clip 216. The saddle 214 is positioned in its modular bump 224 with sufficient clearance above the clip 216 to allow the travel of the spherical head 80 of the screw 14. As shown in FIG. 8C, once the clip 216 passes the center of the spherical head 80 of the screw 14, the modular tulip head 212 has been assembled to the screw 14. Forces directed to dissociate the screw 14 from the modular tulip head 212 translate the clip 216 down against the smaller portion of the groove 222 in the modular head 212, which prevents the clip 216 from expanding to prevent the screw 14 from disassembling from the modular tulip head 212. The saddle is then depressed past the modular bump (as seen in FIG. 9) to further prevent the screw and clip from moving back up and releasing the screw head.

Figure 9:
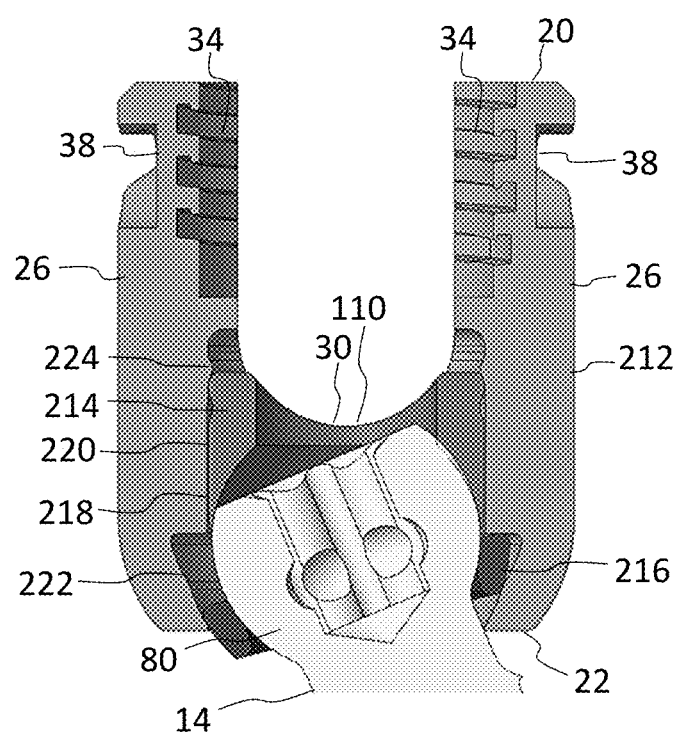
FIG. 9 shows a cross-sectional view of clip angulation according to one embodiment.

FIG. 9 depicts angulation of the screw 14 relative to the modular tulip head 212. In this embodiment, the modular clip 216 and corresponding groove 222 in the tulip head 212 have a spherical profile which allows the clip 216 to angle with the screw head 80, thereby allowing additional angulation. As shown, the screw 14 and clip 216 are angled off-axis, thereby providing for polyaxial movement of the screw 14 relative to the modular tulip head 212. The head assembly and modular head insertion include a simple design easily manufacturable with robust features. The modular bump 224 adds additional security to prevent inadvertent disengagement of the implant 210 and the spherical clip 216 allows additional angulation of the screw head 14.

Turning now to FIGS. 10-13, one or more instrument interfaces may be used for engagement with one or more instruments, such as insertion, positioning, reduction, derotation, compression, distraction and/or other holding instruments. The instrument interfaces allow one or more instruments to fully or partially constrain or attach to the implant, provide increased holding strength, decrease splaying forces which may cause disengagement of the instrument, reduce and lever the rod into position, and/or simplify manufacturing.

Figure 10:
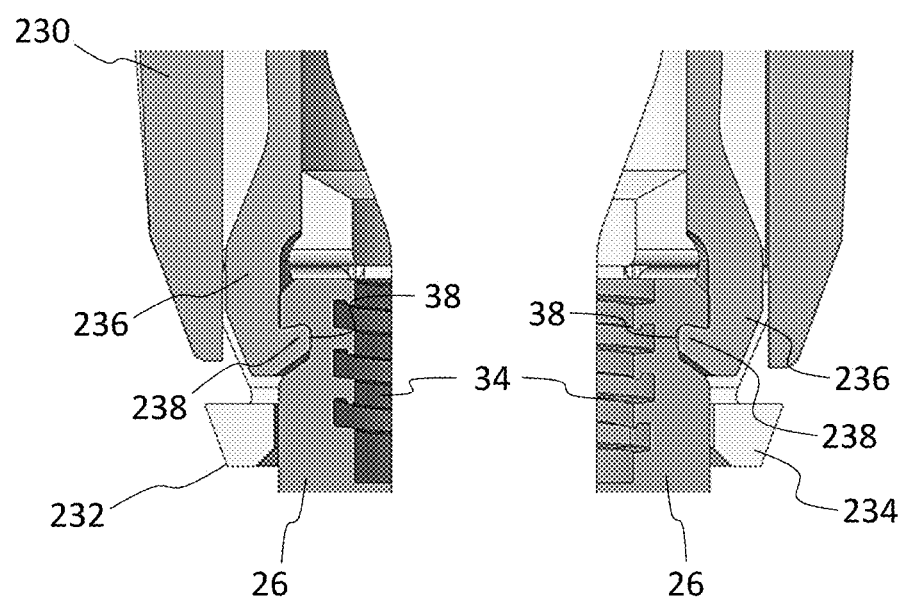
FIG. 10 shows a close-up cross-sectional view of an upper dovetail on the outside of the tulip configured to engage with an instrument section according to one embodiment.

In one embodiment, the annular or cylindrical groove 38 defined into the outer surface 36 of the tulip head 12, 212 provides for engagement of insertion, reduction, derotation, or other holding instrument 230. As shown in FIG. 10, holding instrument 230 may include a distal tip 232 for engaging the proximal end of the tulip head 12, 212. The instrument 230 may have a body or sleeve 234 configured to receive the top of the tulip head 12, 212 and a pair of inner arms 236 with distal prongs 238. The prongs 238 may point toward one another with angled surfaces configured to interface with the groove 38 in the tulip head 12, 212. The interaction between prongs 238 and groove 38 may form a dovetail connection to constrain the instrument 230 axially to the tulip head 12, 212. The inward angle may help to prevent disengagement of the instrument 230 under load by directing forces inward and toward the central axis of the tulip head 12.

Figure 11:
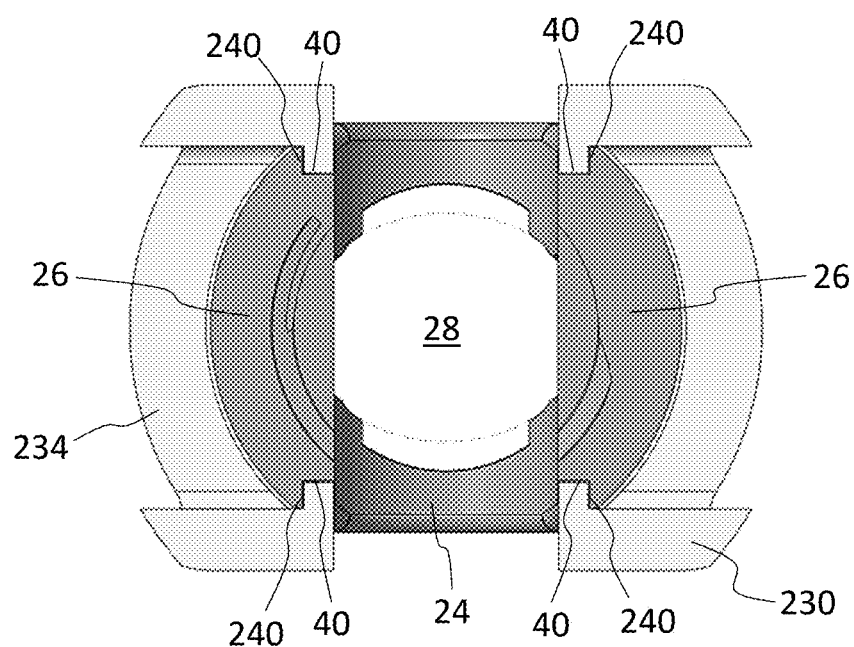
FIG. 11 shows a top view of the tulip and an instrument portion according to one embodiment.

In one embodiment, a plurality of tower pockets 40 are defined into the sides of the arms 26 to prevent splay and disengagement of the instrument 230 from the tulip head 12, 212. As shown in FIG. 11, the sleeve 234 of the holding instrument 230 may include a plurality of protrusions 240 configured to engage with the respective tower pockets 40. For example, the sleeve 234 of the holding instrument 230 may include a first pair of inwardly facing protrusions 240 configured to slidably engage with the first arm 26 and a second pair of inwardly facing protrusions 240 configured to slidably engage with the second arm 26 of the tulip head 12, 212 to constrain rotation of the instrument 230 relative to the tulip head 12, 212. The outward surfaces of the pockets 40 contact corresponding surfaces on the instrument 230, thereby further preventing splay and disengagement of the instrument 230 from the tulip head 12, 212.

Figure 12:
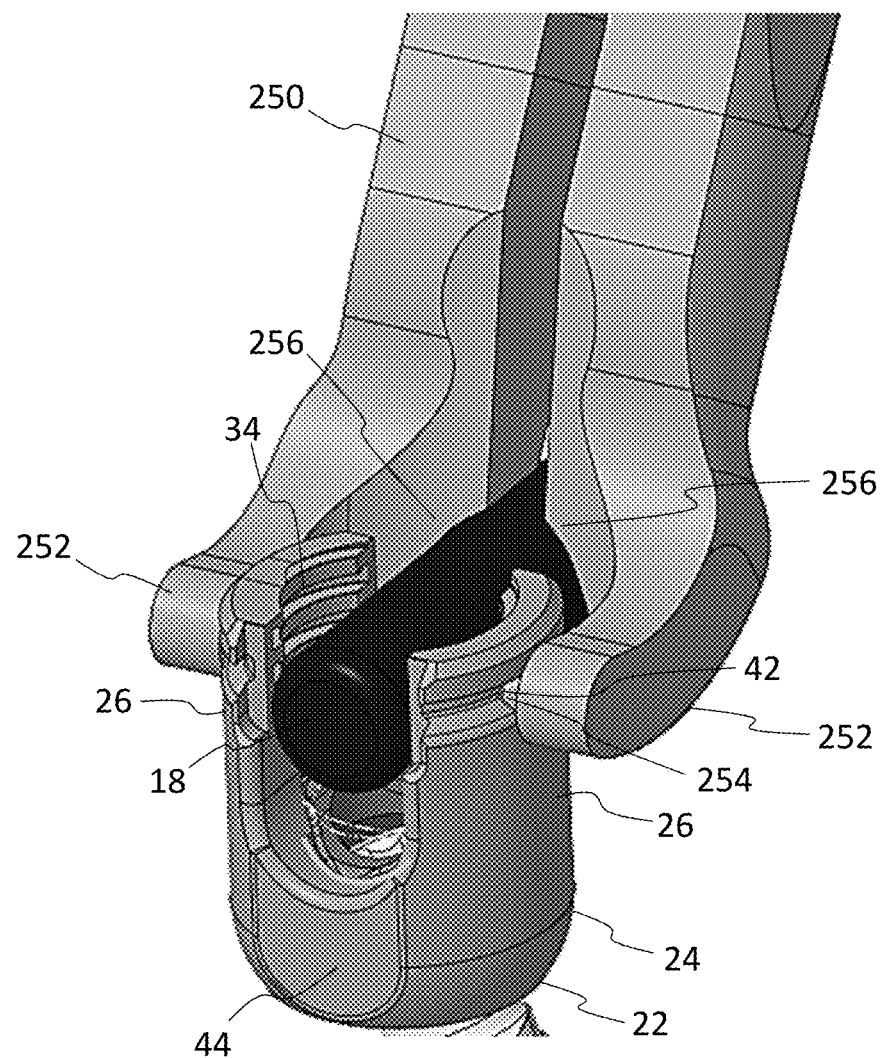
FIG. 12 is a perspective view of the tulip screw assembly engaged with a rocker-style reducer according to one embodiment.

In one embodiment, a pair of rocker holes 42 are defined into the sides of the arms 26 of the tulip head 12, 212 to lever and reduce the rod 18 into the tulip head 12, 212. As shown in FIG. 12, a rocker instrument 250 may include a pair of arm portions 252 positionable on opposite sides of the arms 26 of the tulip head 12, 212. The distal end of each arm portion 252 includes pin 254 receivable in the rocker holes 42. The pins 254 may point inwardly toward one another to engage with the rocker holes 42, thereby allowing for rotation of the instrument 250 within the rocker holes 42. Inner segments of the arm portions 252 include rocker cam surfaces 256 configured to contact the rod 18. The arm portions 252 are configured to grasp the sides of the tulip head 12, 212 with the rocker cam 256 positioned above the rod 18 and then lever backward over the rod 18. The levering action forces the rod 18 to seat into the saddle 90, 214 of the implant 10, 210. Thus, the rod 18 may be levered and reduced into the tulip 12, 212 via engagement of the rocker-style instrument 250 and rotation about the pivot axis of the rocker holes 42 and pins 254.

Figure 13A:
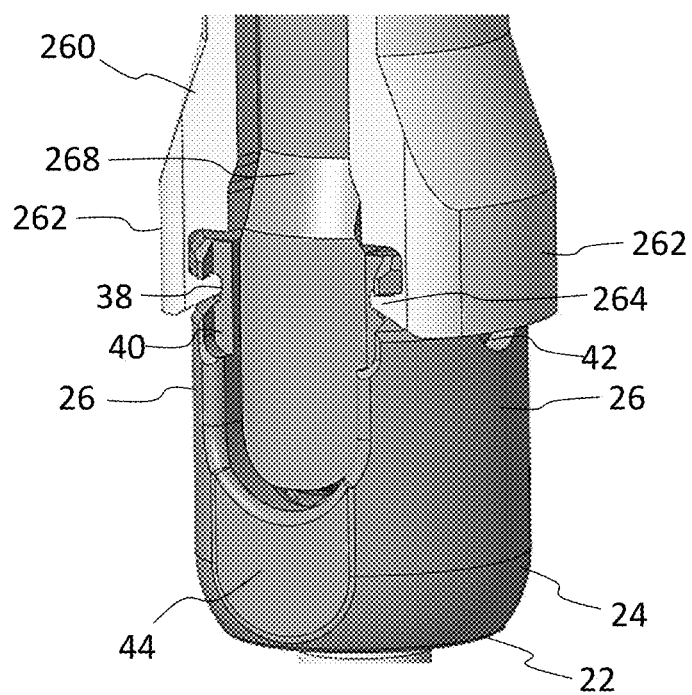
FIGS. 13A-13B show perspective and cross-sectional views, respectively, of a modular head inserter instrument engaged with the tulip head according to one embodiment.
Figure 13B:
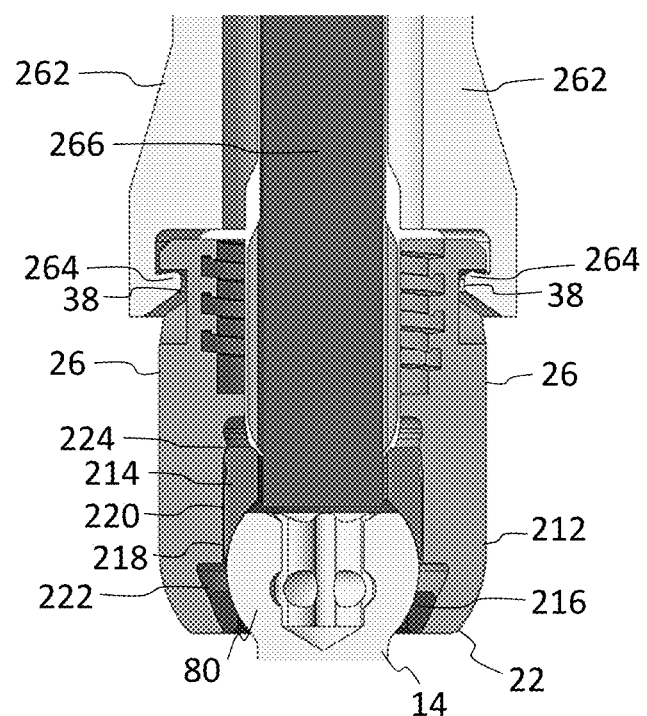

In one embodiment shown in FIGS. 13A-13B, a head inserter instrument 260 may engage the tulip head 12, 212 for insertion. The insertion instrument 260 may include a pair of opposed arm members 262 with distal prongs 264, similar to prongs 238, configured to interface with the groove 38 in the tulip head 12, 212. The arm members 262 and prongs 264 are configured to grasp the sides of the tulip head 12, 212. The interaction between prongs 238 and groove 38 may form a dovetail connection to constrain the instrument 260 axially to the tulip head 12, 212 and prevent disengagement of the instrument 260.

As best seen in FIG. 13B, the insertion instrument 260 may include a displacing pin 266 positioned between the arm members 262 and centered along a central longitudinal axis of the instrument 260. The displacing pin 266 is moveable axially through the arms 262 and is configured to sense the full insertion by contact with the top of the screw head 80. The sensing of the screw insertion unblocks the actuation of the instrument 260, which permits a pusher 268 to displace downward and depress the saddle 214 past the modular bump 224. The pusher 268 may include a pair of pusher blades oriented 90° relative to arms 26 and configured to fit in the gap therebetween. The pusher 268 restricts the screw head 80 and clip 216 from translating upward to prevent the clip 216 from expanding and releasing the screw head 80 while the inserter instrument 260 is attached. The instrument engagement features may help to prevent instrument disengagement under high loads while maintaining a low instrument and implant profile away from bony anatomy.

Figure 14A:
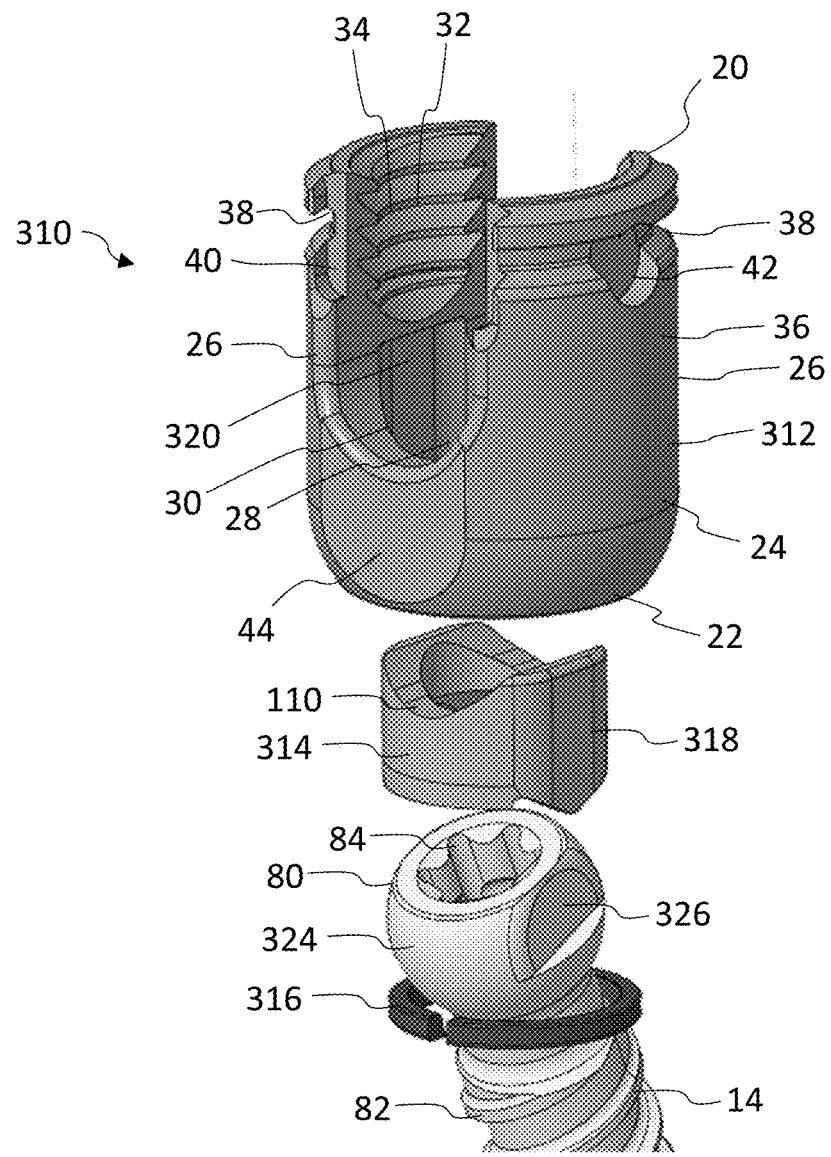
FIGS. 14A-14B show exploded and close-up cross-sectional views, respectively, of a uniplanar screw according to one embodiment.
Figure 14B:
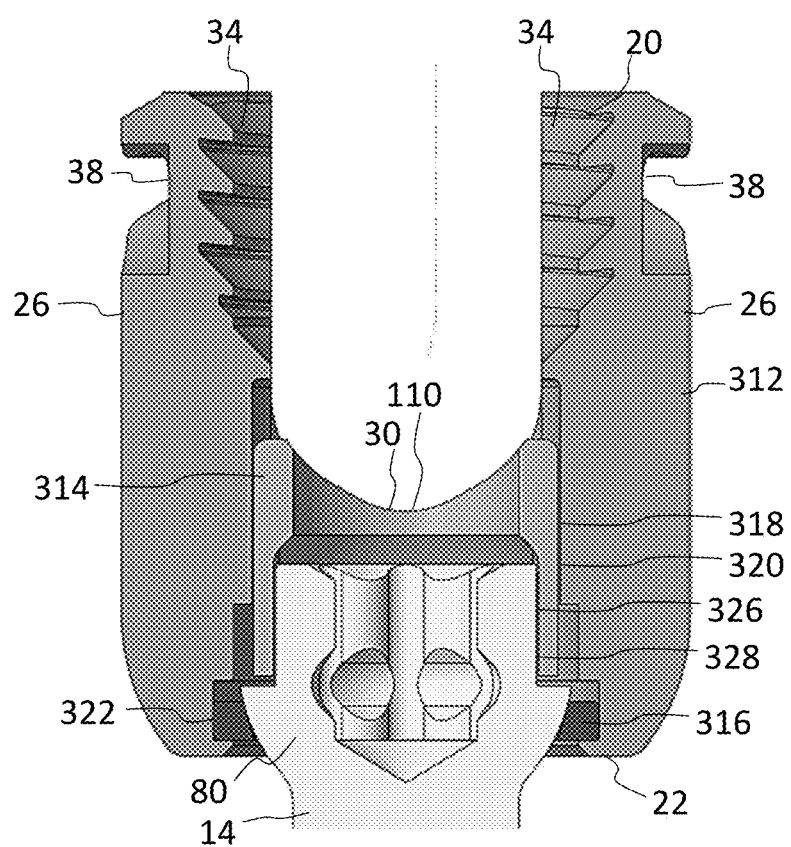

Turning now to FIGS. 14A-14B, the tulip head 12, 212 may also be applied to other screw designs, such as uniplanar and monoaxial screws. FIGS. 14A-14B show one embodiment of a uniplanar screw assembly 310 (a close-up exploded view and cross-sectional view is shown with the distal end of the screw shaft omitted for clarity). In this embodiment, the uniplanar pedicle screw assembly 310 allows for angulation in one direction but not the other direction. The uniplanar movement allows the application of forces through the screw rigidly for correction of spinal deformities. Similar to the polyaxial screw assembly 210, the uniplanar screw assembly 310 includes a tulip head 312, a saddle 314, and a clip 316 for retaining the screw head 80 of a uniplanar screw. Tulip head 312 has many of the same features as tulips 12, 212 including opposed arms 26 defining U-shaped rod slot 30 configured to accept the rod 18, interior threaded portions 34 for engaging the locking cap 16, and one or more outer engagement features 38, 40, 42, 44 for interaction with mating instruments. The tulip head 312 provides for benefits similar to the polyaxial screw assembly 12, 212, which enables re-use of existing tooling and fewer complicated manufacturing steps.

The head component 312 houses the saddle 314 and clip 316. The saddle 314 includes upper seat 110 for receiving the rod 18 and a bottom surface for receiving the top of the screw head 80. Opposite sides of the saddle 314 have flat surfaces 318 configured to mate with corresponding flat surfaces 320 inside the tulip head 312. The flats 320 in the tulip head 312 may be positioned inside each arm 26 below the threaded portion 34. The mating flat surfaces 318, 320 on the outside of the saddle 314 and inside head 312 restrict the saddle 314 from angling within the tulip 312.

The clip 316 may include a loop, ring, split-ring, snap ring, or other suitable retaining ring. In an exemplary embodiment, the clip 316 is a split retaining clip. The clip 316 rests in a groove 322 in the base of the tulip 312 and is configured to fit around the bottom of the screw head 80. The clip component 316 retains the bone screw 14 within the assembly 310 and resists compressive force exerted down on the bone screw 14.

In this embodiment, the screw head 80 includes spherical surfaces 324 in the direction of motion (e.g., aligned with the rod 18), and flat opposing surfaces 326 parallel to the direction of angulation, which restrict angulation in the perpendicular direction. The flat surfaces 326 of the head 80 align with corresponding flat surfaces 328 inside the saddle 314. These flat surfaces 326, 328 restrict rotation of the bone screw 14 about the central axis of the tulip 312. Orientation of the flat surfaces 326, 328 in the saddle 314 perpendicular to the view shown in FIG. 14B results in the restriction of angulation in the opposite direction. In particular, the flats 326, 328 restrict medial-lateral angulation for uniplanar functionality.

The tulip head 312 pivots on the screw head 80 in one direction (e.g., medial-lateral angulation). It will be appreciated that the tulip head 12 is permitted to pivot either along the rod slot 30 or perpendicular to the rod slot 30 depending on the configuration of the components. The orientation of the flat surfaces 326, 328 parallel to the rod slot 30 results in a uniplanar screw able to control coronal and axial corrections. The orientation of these surfaces 326, 328 perpendicular to the rod slot 30 results in a uniplanar fracture screw able to control sagittal corrections commonly used in correcting traumatic fractures.

When the saddle 314 is in an upward position, the saddle 314 is able to accept the screw head 80 and allows the insertion of clip 316 which retains the screw head. As shown in FIG. 14B, when the saddle 314 is then translated downward within the tulip head 162, the screw head 80 is retained within the tulip assembly. The saddle 314 compresses against the head 80 of the screw when threaded locking cap 16 is threaded downwardly onto the spinal rod 18, thereby pushing against the saddle 314. The saddle 314 applies compressive force to the bone screw 14 and restricts its angulation when the rod 18 is tightened to the implant 310 with the locking cap 16. In this locked position, the uniplanar screw assembly 310 is locked in place, thereby restricting motion.

The devices and assemblies described herein may allow for improved functionality, strength, and ease of manufacturing for pedicle screw head assemblies. The component features may simplify geometries to reduce profile, increase strength, and/or simplify manufacturing and assembly.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. An orthopedic fixation assembly comprising:
 a tulip head having two arms defining a rod slot therebetween and a bore extending therethrough;
 a saddle receivable in the bore of the tulip head, the saddle having an upper surface defining a rod seat aligned with the rod slot;
 a bearing washer positionable below the saddle;
 a shear clip positionable over the bearing washer; and
 a support clip configured to retain the shear clip in the tulip head, wherein the shear clip is breakable at a fracture site upon application of a force,
 wherein the bearing washer is configured to center the shear clip within the tulip head to limit translation.

2. The orthopedic fixation assembly of claim 1, wherein the shear clip has three states including an initial solid form, an expanded form after the shear clip breaks, and a collapsed form.

3. The orthopedic fixation assembly of claim 2, wherein in the initial solid form, the shear clip is a full ring with partial slits defining a temporary bridge portion.

4. The orthopedic fixation assembly of claim 3, wherein in the expanded form after the shear clip breaks, the bridge portion breaks, thereby separating the full ring into a split ring radially expanded outward.

5. The orthopedic fixation assembly of claim 4, wherein in the collapsed form, the split ring collapses and springs closed.

6. The orthopedic fixation assembly of claim 1, wherein the bearing washer includes a split ring with a radial neck protruding outward from the split ring.

7. The orthopedic fixation assembly of claim 1, wherein the support clip includes a split ring configured to fit in an internal groove at a bottom of the tulip head.

8. An orthopedic fixation assembly comprising:
 a tulip head having two arms defining a rod slot therebetween, each of the arms defining a threaded portion along an interior surface, the tulip head having a bore extending therethrough;
 a breakable shear clip positioned in the bore of the tulip head; and
 a bone fastener including a screw head receivable in the tulip head and a shaft configured for engaging bone,
 wherein the breakable shear clip has an initial solid form, and when the bone fastener is loaded into the tulip head, the shear clip breaks forming a split ring that expands radially outward to accept the screw head, and then the shear clip collapses around the screw head, thereby securing the bone fastener to the tulip head
 wherein a bearing washer housed in an internal groove in the tulip head, the bearing washer including a split ring with a radial neck protruding outward from the split ring and a plurality of slits defined through the top of the neck downward into the split ring.

9. The orthopedic fixation assembly of claim 8, wherein the initial solid form of the shear clip is a full ring defining an inner seat for receiving the bearing washer and a predefined fracture site configured to break upon application of a force by the bone fastener.

10. The orthopedic fixation assembly of claim 8 further comprising a support clip for retaining the shear clip within the tulip head, the support clip includes a split ring defining a seat for the shear clip.

11. The orthopedic fixation assembly of claim 10, wherein after the shear clip collapses around the screw head, the shear clip rests in the seat of the support clip and presses against the screw head.

12. The orthopedic fixation assembly of claim 8 further comprising a saddle having an upper surface defining a rod seat and lower portion configured for receiving the screw head.

13. The orthopedic fixation assembly of claim 12 further comprising a locking cap having an outer body defining a thread, wherein the locking cap is threadable between the two arms of the tulip head to secure a rod therein.

14. The orthopedic fixation assembly of claim 13, wherein when the locking cap is threaded downwardly onto the rod, the rod pushes against the rod seat of the saddle, and the saddle secures the bone fastener.

\* \* \* \* \*